US009695072B2

(12) United States Patent
Milosevic et al.

(10) Patent No.: US 9,695,072 B2
(45) Date of Patent: Jul. 4, 2017

(54) MONITORING APPARATUS AND SYSTEM

(71) Applicants: Milan Milosevic, Westport, CT (US); Matthew Higgins, Geneva, NY (US); Stephen J. Ho, Putnam Valley, NY (US)

(72) Inventors: Milan Milosevic, Westport, CT (US); Matthew Higgins, Geneva, NY (US); Stephen J. Ho, Putnam Valley, NY (US)

( * ) Notice: Subject to any disclaimer, the term of this patent is extended or adjusted under 35 U.S.C. 154(b) by 259 days.

(21) Appl. No.: 14/610,364

(22) Filed: Jan. 30, 2015

(65) Prior Publication Data

US 2016/0223452 A1 Aug. 4, 2016

(51) Int. Cl.
| | |
|---|---|
| C02F 1/52 | (2006.01) |
| G03B 17/56 | (2006.01) |
| C02F 1/00 | (2006.01) |
| G03B 17/08 | (2006.01) |
| G01N 15/02 | (2006.01) |
| G03B 15/03 | (2006.01) |
| G01N 15/14 | (2006.01) |
| H04N 5/225 | (2006.01) |
| G01N 15/00 | (2006.01) |

(52) U.S. Cl.
CPC ............ *C02F 1/5209* (2013.01); *C02F 1/008* (2013.01); *G01N 15/0227* (2013.01); *G03B 15/03* (2013.01); *G03B 17/08* (2013.01); *G03B 17/561* (2013.01); *C02F 2209/005* (2013.01); *C02F 2209/06* (2013.01); *C02F 2209/11* (2013.01); *G01N 2015/0053* (2013.01); *G01N 2015/0092* (2013.01); *H04N 5/2256* (2013.01)

(58) Field of Classification Search
CPC .. C02F 1/5209; C02F 2209/005; C02F 1/008; C02F 2209/06; C02F 2209/11; G01N 15/0227; G01N 2015/0053; G01N 2015/0092; H04N 5/2252; H04N 5/2256; G03B 17/08; G03B 17/561
See application file for complete search history.

(56) References Cited

U.S. PATENT DOCUMENTS

| | | | |
|---|---|---|---|
| 3,827,068 | A | 7/1974 | Hill, Jr. |
| 5,287,133 | A | 2/1994 | Bohley |
| 6,882,412 | B2 | 4/2005 | Silverman |
| 7,409,853 | B2 | 8/2008 | Biberger |
| 7,484,468 | B2 | 2/2009 | Russell |

(Continued)

FOREIGN PATENT DOCUMENTS

JP S62289061 12/1987

*Primary Examiner* — Sath V Perungavoor
*Assistant Examiner* — Howard D Brown, Jr.
(74) *Attorney, Agent, or Firm* — Michael A. Blake

(57) ABSTRACT

A floating monitoring apparatus and system comprising: a base; a first flotation device attached to the base and located generally below the base, the flotation device configured to float on a surface of water; a light support member extending downward from the base, and configured to be at least partially below the surface of water; a camera attached to the base and configured to be aimed to capture images of a target below the base, where the camera is generally kept above the surface of the water; a light source attached to the light support member, and configured to direct light to illuminate the target, the lights located below the surface of the water.

13 Claims, 4 Drawing Sheets

(56) References Cited

U.S. PATENT DOCUMENTS

| | | |
|---|---|---|
| 8,293,097 B2 | 10/2012 | Bowers, Jr. |
| 8,459,100 B2 | 6/2013 | Biberger |
| 8,506,799 B2 | 8/2013 | Jorden |
| 8,755,683 B2 | 6/2014 | Biesse |
| 2008/0248703 A1* | 10/2008 | Russell ............... B63B 1/10 441/136 |
| 2011/0094433 A1* | 4/2011 | Shoda ............... B63C 11/42 114/330 |
| 2013/0107031 A1* | 5/2013 | Atkinson .......... H04N 1/00347 348/81 |
| 2013/0315577 A1* | 11/2013 | Clark ............... G03B 17/561 396/27 |
| 2013/0335731 A1 | 12/2013 | Jorden |
| 2014/0111642 A1 | 4/2014 | Tzonev |
| 2016/0026071 A1* | 1/2016 | Kanai ............... G03B 17/08 396/25 |
| 2016/0119065 A1* | 4/2016 | Tobias ............... G03B 17/08 348/81 |

* cited by examiner

MONITORING APPARATUS AND SYSTEM

TECHNICAL FIELD

The invention relates to a monitoring apparatus, and more particularly, to a monitoring apparatus with a camera and a light source.

BACKGROUND

In its path through the environment, water dissolves many substances and suspends many others. The type and concentration of these impurities vary greatly depending upon the source of the water, the environment through which it passes and the regional climate. These particles may be made up of clay, algae, silt, organic and inorganic colloids, and microbes. The initial stages of water treatment may be designed to remove as many of the suspended particles as possible, thereby preparing the water to be filtered. If such material is not removed before filtration, it may reduce the effectiveness of, and eventually clog, the filters. Disruption of the filters may render the water treatment process ineffective.

Water treatment generally has several stages. The first stage may be coagulation. During coagulation, a chemical, such as polyaluminum chloride, may be rapidly mixed into the water. This chemical may neutralize the (typically negative) electrical charges that are present on the small, suspended particles.

The next stage may be flocculation. During flocculation, the water is gently mixed to increase the number of collisions between the small, suspended particles. The colliding particles, which may have been neutralized due to effective coagulation, may stick together to form larger particles called flocs. The goal of flocculation is to create flocs that will rapidly settle out of the water, thereby reducing the number of impurities present in the remaining water. The leftover water may then be filtered to remove any remaining particles.

In addition to the design of the settling basin, physical characteristics of the flocs, including their size, density and shape, are significant in determining the flocs' settling rate. Thus, it would be advantageous to the water treatment process if these parameters were monitored during flocculation to enable optimization of the process's operational parameters including concentration of coagulant and coagulant-aid chemicals and the intensity of mixing of water.

The aforementioned physical characteristics may be challenging to monitor using standard methods including systematic sampling and flow-through monitoring. In this context, systematic sampling may refer to the collection of a volume of water at regular intervals for analysis. This type of systematic sampling necessitates additional resources (personnel and time) and may disturb the particles during treatment. Flow-through monitoring may refer to a system in which a stream of water is diverted to a cuvette for analysis. This method is problematic because flocs may break due to the flow patterns in the sampling device. In addition, the size of the tubing and cuvette limit the size of flocs that can be analyzed.

There is no known automatic process or system that can monitor, and evaluate the size, density, and type of floc and/or other material in the water in situ during treatment.

Thus there is a need for an apparatus and system that can overcome the above listed and other challenges and disadvantages.

SUMMARY OF THE INVENTION

The disclosed invention relates to a floating monitoring apparatus comprising: a base; a first flotation device attached to the base and located generally below the base, the flotation device configured to float on a surface of water; a light support member extending downward from the base, and configured to be at least partially below the surface of water; a camera attached to the base and configured to be aimed to capture images of a target below the base, where the camera is generally kept above the surface of the water; a light source attached to the light support member, and configured to direct light to illuminate the target, the lights located below the surface of the water.

The invention also relates to a floating monitoring system comprising: a volume of water; a base, configured to be located generally above the surface of the volume of water; a first flotation device attached to the base and located generally below the base, the flotation device configured to float on the surface of water; a light support member extending downward from the base, and configured to be at least partially below the surface of water; a camera attached to the base and configured to be aimed to capture images of a target below the base, where the camera is generally kept above the surface of the water; a light source attached to the light support member, and configured to direct light to illuminate the target, the lights located below the surface of the water; a rod, with a first end and a second end, the first end of the rod rotatably attached to the base; a structure located outside of the volume of water, the second end of the rod rotatably attached to the structure.

In addition, the invention is related to a monitoring apparatus comprising: a base configured to sit on top of a jar; a first side extending downwardly from the base, and configured to be located on the outside of the jar; a second side extending downwardly from the base, and configured to be located on the outside of the jar; a third side extending downwardly from the base, and configured to be located on the outside of the jar; a camera housing located on the first side; a camera located in the camera housing, the camera configured to view a target located inside the jar; a light source located on the second side, the light source configured to illuminate a target inside the jar; where the light source and camera are configured such that light emanating from the light source is generally orthogonal to the field of view of the camera.

BRIEF DESCRIPTION OF THE DRAWINGS

The present disclosure will be better understood by those skilled in the pertinent art by referencing the accompanying drawings, where like elements are numbered alike in the several figures, in which.

DETAILED DESCRIPTION

Figure 1:
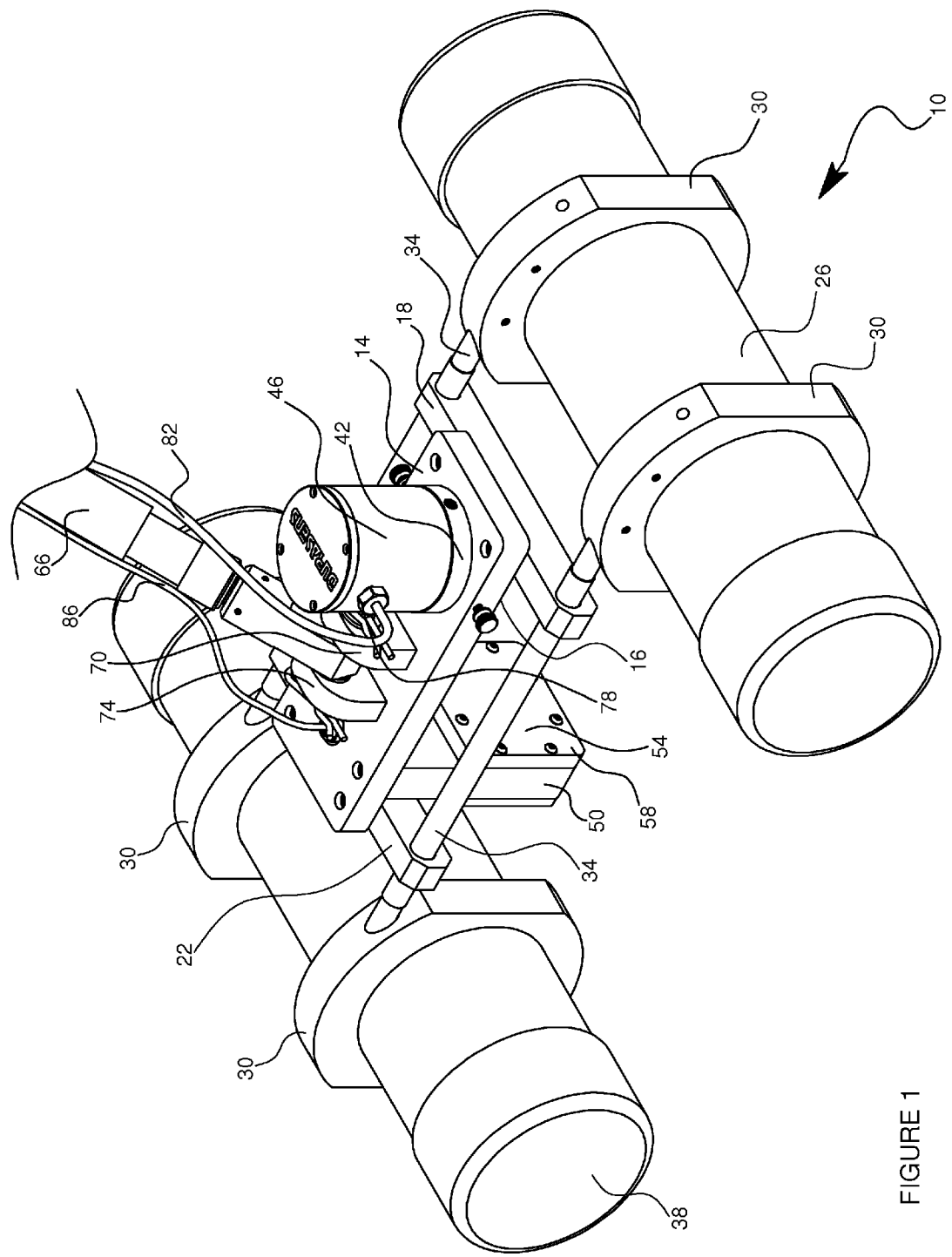
FIG. 1 is a perspective view of the disclosed apparatus.

FIG. 1 is a perspective view of one embodiment of the floating monitoring apparatus 10. The apparatus 10 comprises a base 14. The base 14 comprises two attachment members 18, 22 generally on opposite ends of the base 14. A first flotation device 26 is attached to at least one flotation holder 30. The flotation holders 30 are attached to at least one flotation connecting member 34. The flotation connecting members 34 are attached to both flotation attachment members 18, 22. A second flotation device 38 may be located generally opposite of the base 14 from the first flotation device 26. The second flotation device 38 is attached to at least one flotation holder 30. The flotation holders 30 are attached to at least one flotation connecting member 34. The flotation devices 26, 38 may be any suitable floating device, including but not limited to the shown pontoon style flotation devices. Attached to the base is a camera 42. The camera 42 is located generally on top of the base and will be kept out of the water when the apparatus 10 is floating on the water's surface. The camera 42 is configured to look down through a camera hole 62 in the base 14 and see a target that will generally be below the surface of the water. The hole 62 is not visible in this view. The camera hole 62 is visible in FIG. 2. The camera may be in a waterproof housing 46. A light support member 50 extends from the bottom 16 of the base 14. One or more light sources 54 are located inside the light support member 50. The light sources 54 are configured to illuminate the target that the camera 42 is configured to record. The light sources 54 may be enclosed in a waterproof housing 58. The housing 58 may have a transparent or translucent window to allow light from the light sources 54 to illuminate the target. The light sources 54 may be any suitable lighting device, including but not limited to LED lights, fluorescent lamps, incandescent lights, and halogen. A rod 66 may be attached to the base 14. The rod 66 may be extendible, telescoping, or of a single length. The rod 66 may be rotatably attached to the base 14. In one embodiment, the base 14 may have two rod attachment members 70, 74. One end of the rod 66 may be located between the two rod attachment members 70, 74, and a pin 78 may go through the two rod attachment members 70, 74 and the one end of the rod 66, to allow the rod 66 to rotate with respect to the base 14. In one embodiment, the camera 42 and light sources 54 may each have their own power supply. The camera may be in wireless communication with a network, where the images obtained by the camera may be communicated to the network. In another embodiment, the camera 42 may be connected to a remote power supply located some distance away from the base 14. The camera 42 may be connected to the remote power supply via a cable or wire 82. Similarly, the light sources 54 may also be connected to a remote power supply via a cable or wire 86. The cables or wires 82, 86 may travel up the rod 66 to a remote power supply. The cable or wire 82 may also communicate electronic images from the camera to a network, Wi-Fi transmitter, or a computer.

Figure 2:
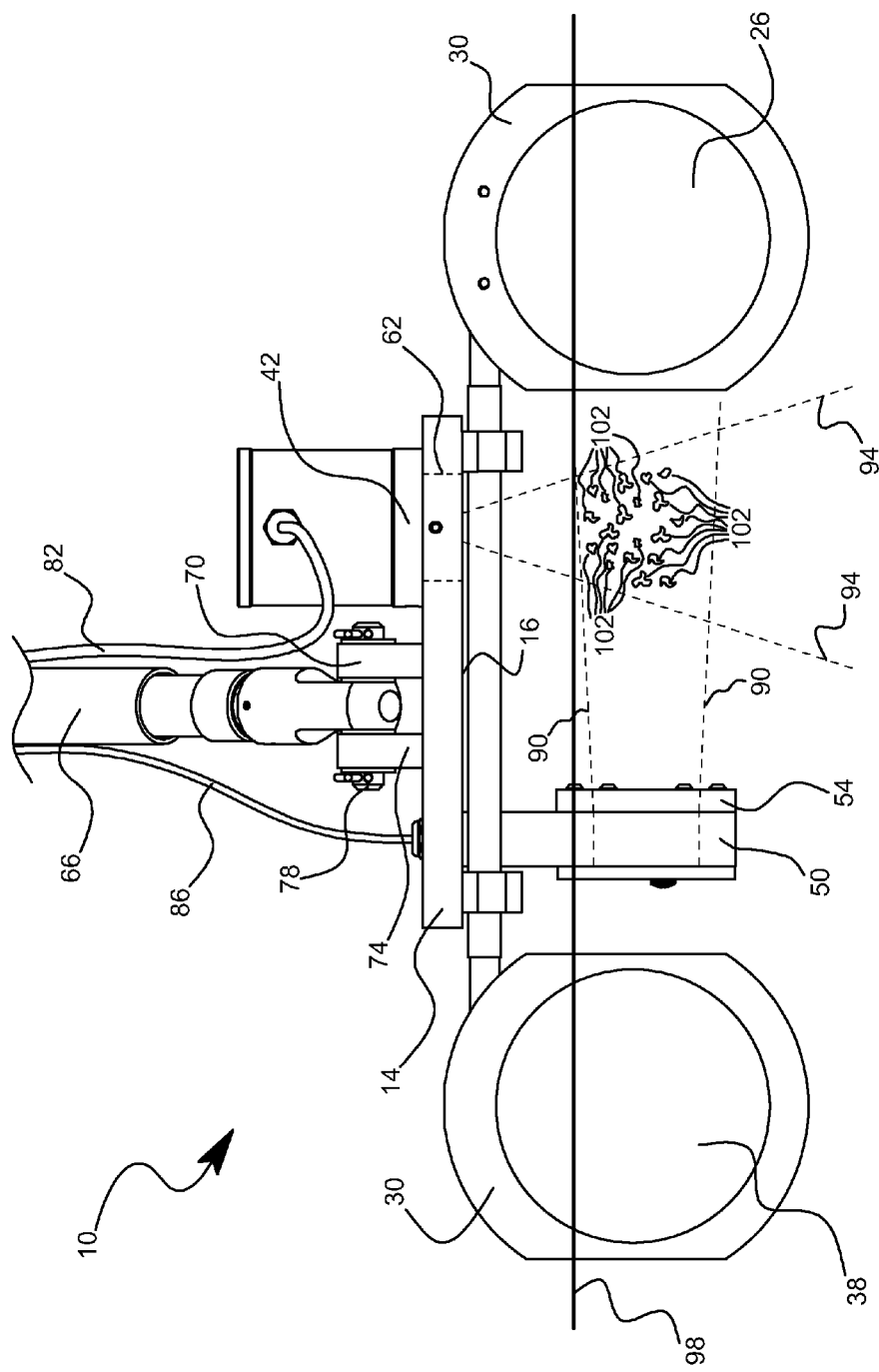
FIG. 2 is a side view of the base from the disclosed apparatus.

FIG. 2 is a side view of the base 14 from FIG. 1. Light emanating from the light sources 54 are shown by the lines 90. The field of view of the camera 42 is represented by the lines 94. The water surface is represented by line 98. As can be seen, the field of view of the camera is aimed below the base 14 below the surface of the water and is able to capture images of the targets 102. The targets may be any particles in the water, including but not limited to floccules (flocs). The targets are illuminated by the light from the light sources 54. The light sources 54 are beneath the surface of the water, and the camera 42 is above the surface of the water. Please note that the light emanating from the light sources 54 is generally orthogonal to the field of view of the camera 42.

Figure 3:
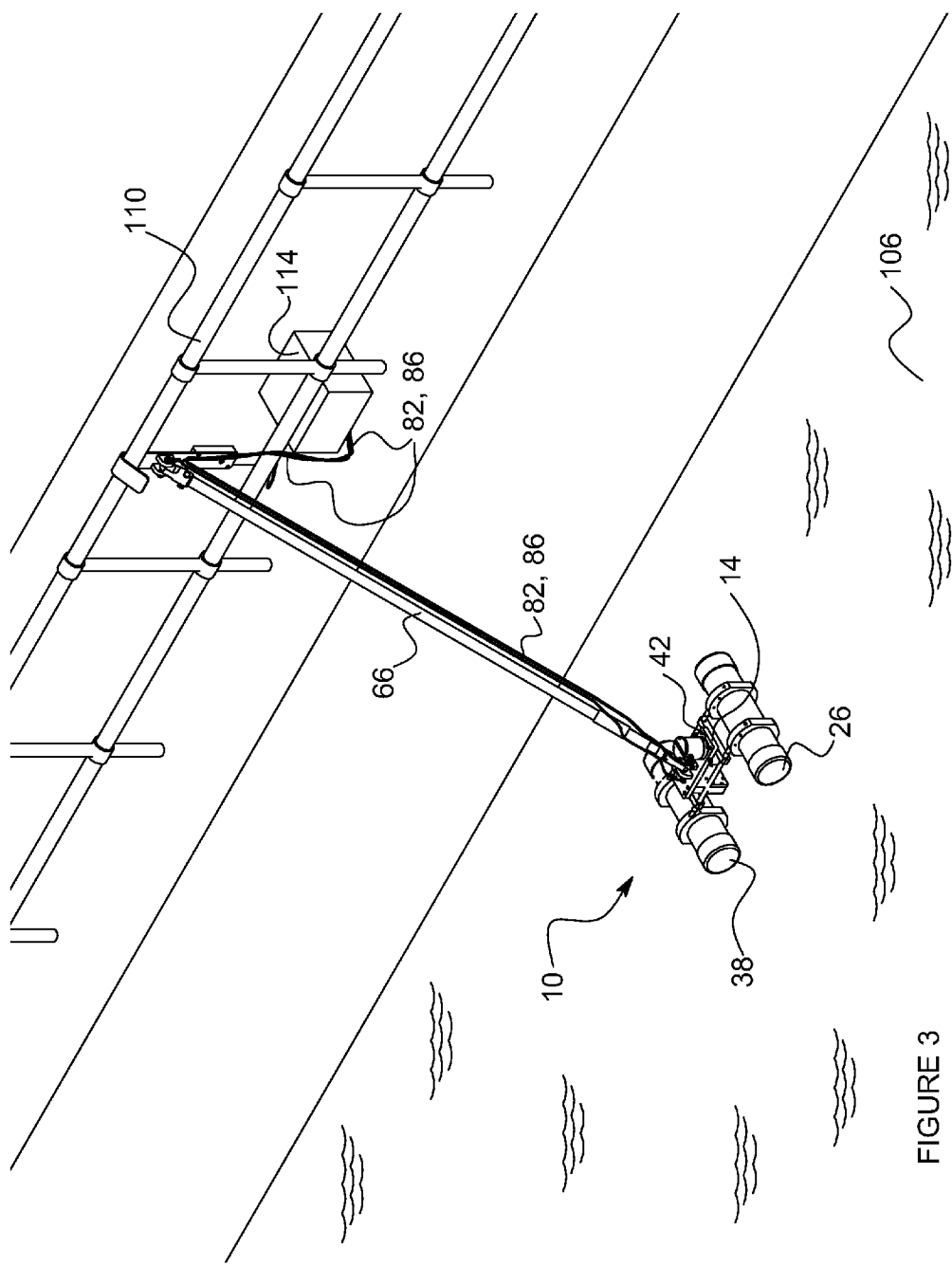
FIG. 3 is a schematic view of the disclosed system.

FIG. 3 shows the floating monitoring apparatus 10 floating in a body of water 106, such as but not limited to a water treatment pond, pool, basin, clarifier, or water tank. The rod 66 is connected to a fence 110 in this embodiment, but in other embodiments, the rod may be connected to a railing, post, wall of a tank or any other suitable structure. Located near the post may be a power supply 114. In other embodiments, the power supply may include a Wi-Fi transmitter in communication with a computer network, or a wired connection to a network. In still other embodiments, the power supply 114 may include a computer to receive the images from the camera 42.

The disclosed floating monitoring apparatus and system is an instrument generally devised for in-situ monitoring of floc particles during various water treatment processes. In this context, a floc particle is an aggregated mass of suspended and/or precipitated material that is typically generated during the process of flocculation. The disclosed floating monitoring apparatus may float on the surface of a tank within a water or wastewater treatment plant and provide real-time data indicating the physical properties and motion of particles during the treatment process. The camera system's innovative design is specifically tailored to function within a typical treatment plant environment. The included mounting hardware is easily adaptable to all types of tank-side railings for simple and quick installation. The apparatus' pontoon floats, which may be made out of PVC, ensure that the treatment process remains undisturbed and the unit only minimally contacts the water. Furthermore, the disclosed floating monitoring apparatus and system's electronic components are physically shielded from the surrounding environment to protect them from the humidity and temperature typically present within a treatment plant. Once installed in the tank, the floating monitoring apparatus and system may be operated with an easy-to-use computer program. The program collects and displays' real-time data regarding the number and average diameter of floc particles, the overall particle size distribution and average particle velocity and density. It is optimized to characterize the full range (about 0.25 mm to about 15 mm) of particle sizes present during typical flocculation. The collected data may be stored in an easily accessible file for analysis and comparison with past and future plant operation. The disclosed floating monitoring apparatus and system enables operators to immediately detect changes during flocculation caused by a change in the incoming water quality, an addition, or change in the dose, of coagulants and any other chemical, as well as a change in the flow regime due to an alteration of impeller rotational speed. The ability to clearly detect the effects of these changes gives the operator an improved understanding of the water treatment plant's current operation.

Traditionally, the appropriate dose of chemical(s) to optimize coagulation and flocculation is determined by a laboratory test. This test is designed to imitate the coagulation and flocculation processes that occur in the treatment basins. In this test, which may be called a jar test, several standard rectangular jars are filled with untreated water. Each jar is then administered a different dose of the chemical(s) used during coagulation. The solution within each jar is then agitated in the same manner as if it was flowing through the plant: it is vigorously mixed for a short period of time, followed by a longer period of slow mixing that encourages flocculation. After a certain period of time, the mixing is stopped and the operator often subjectively observes, in each jar, the physical characteristics of the floc particles and their settling speed. After the settling period, the operator may collect a water sample and measure water quality characteristics such as turbidity, color and pH. Due to the initial variation in chemical dose administered to the untreated water within the jars, the user can compare the test results from the jars to determine the chemical dose that optimizes the treatment plant's coagulation and flocculation processes.

A variation of the disclosed device can be made that mounts to the standard jar test vessel and monitors and records data regarding the same parameters (size, density, shape) analyzed in situ in the flocculation basin during treatment. Use of this version of the disclosed device provides user with a complete record of the jar test. All of the data collected during ajar test is quantified and stored in a file to facilitate an objective, data-based comparison of the test results. The variant of present invention intended for use in ajar test is depicted in FIGS. 4 and 5.

Figure 5:
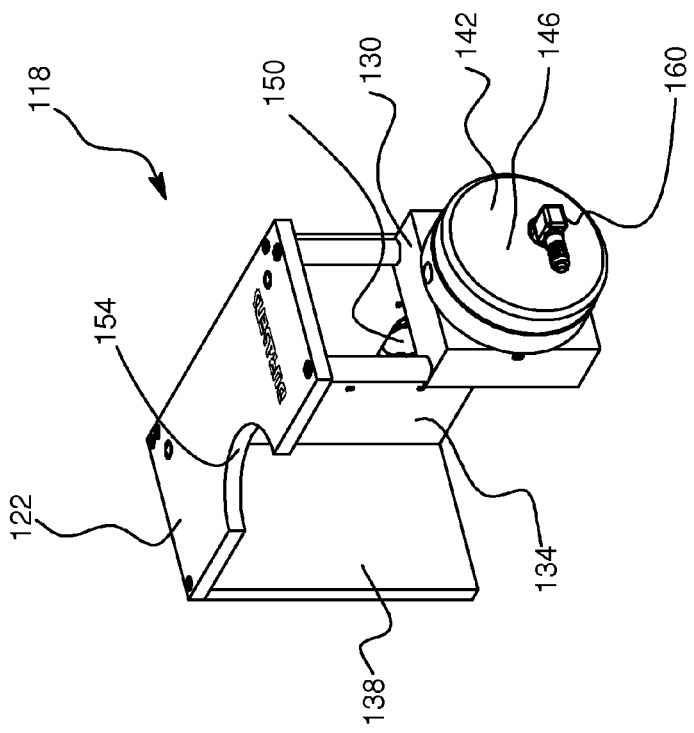
FIG. 5 is an additional perspective view of the embodiment of the monitoring apparatus system shown in FIG. 4.
Figure 4:
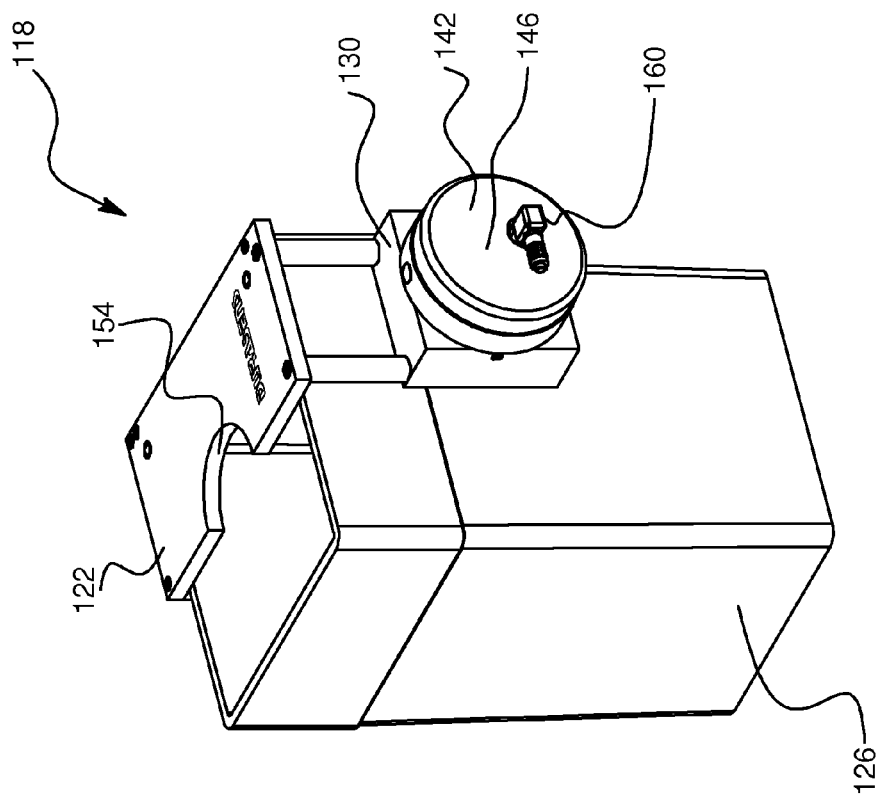
FIG. 4 is a perspective view of another embodiment of the monitoring apparatus and system.

FIGS. 4 and 5 show another embodiment of the monitoring apparatus and system 118. FIG. 4 shows the apparatus 118 sitting on top of a jar 126. FIG. 6 shows the apparatus 118 without the jar. The apparatus 118 comprises a base 122 configured to sit on top of a jar 126. The base is attached to a first side 130, a second side 134, and a third side 138. The base 122, and three sides 130, 134, 138 are configured to be generally on the outside of the jar, with the base 122 generally resting on the top of the jar 126. In this embodiment, the jar will generally be optically transparent. The first side 130 comprises a camera housing 142. Located inside the camera housing 142 is a camera 146 that is configured to look into the jar 126 and record a target located in the jar 126. The first side 130 will have an opening or an area that allows a clear line of view from the camera 146 into the jar 126. The second side 134 comprises a light source 150. The light source 150 may be any suitable lighting device, including but not limited to LED lights, fluorescent lamps, incandescent lights, and halogen. The light source 150 is configured to illuminate the target inside the jar 126 that the camera 146 is configured to record. The third side 138 is configured to help hold the apparatus 118 to the jar 126. In other embodiments, the apparatus 118 may have a fourth side, to provide an even more secure attachment to the jar 126. The base 122 may have clearance opening 154 cut or otherwise manufactured into the base. The clearance opening 154 is configured to make it easier to insert a stirrer and stir the contents of the jar 126, especially near the camera 146 and light source 150 target volume. The apparatus 118 may comprise a power source for the light source 150 and camera 146. In other embodiments, an external power source may be in communication with the light source 150 and camera 146. The camera 146 may be in signal communication with a computer, either through a network, or directly with a computer. A connector 160 may extend from the camera housing 142, and may be configured to connect the camera to computer and/or light source. Please note that the light emanating from the light source 150 is generally orthogonal to the field of view of the camera 146.

The disclosed floating monitoring apparatus and system has many advantages. The hinged or rotatable attachment at each end of the rod allows the base and flotation devices to float generally freely in the water. The camera is generally kept above the surface of the water, thereby keeping the camera free from the harsh environment of being submerged, allowing for a much longer lifespan for the camera. The light sources are below the surface of the water, and direct light towards the targets being recorded by the camera. The system allows monitoring of the flocs and other particles in the water by the system, without the need for a human operator to visit the water tank, basin, pond, etc., and make observations of the flocs or other particles in the water. Because the system has its own light source, the particles can be viewed at night, or in an enclosed tank with no other light source. The design of the apparatus is relatively simple and to the device can be manufactured inexpensively. The flotation devices may be simple pontoon flotation devices, also easy to manufacture and/or adapt to the disclosed apparatus and system. The system allows for real-time monitoring of the size distribution, shape, number, and other quantitative parameters of floc particles. These parameters can then be used to provide feedback to plant's process control software to optimize the amount of chemicals added to the water as well as the speed of mixing of the water. The advantage of this feedback system is that it enables optimization of the flocculation process. An optimized flocculation process minimizes the filter clogging during the filtering stage, minimizes the amount, hence expense, of chemicals used, and minimizes the amount of sludge (settled floc plus added chemicals) that has to be disposed of as chemical waste, an expensive operation.

It should be noted that the terms "first", "second", and "third", and the like may be used herein to modify elements performing similar and/or analogous functions. These modifiers do not imply a spatial, sequential, or hierarchical order to the modified elements unless specifically stated.

While the disclosure has been described with reference to several embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for carrying out this disclosure, but that the disclosure will include all embodiments falling within the scope of the appended claims.

What is claimed is:

1. A floating monitoring apparatus comprising:
a base, the base comprising an opening rigidly located in the base;
a first flotation device nonrotatably attached to the base and located generally below the base, the flotation device a non-inflatable rigid pontoon style flotation device configured to float on a surface of water, wherein the base is configured to be nonrotatable with respect to the flotation device;
a light support member extending downward from the base, and configured to be at least partially below the surface of water;
a camera nonrotatably attached to the base and configured to be aimed through the opening to capture images of a target below the base, wherein the camera is generally kept above the surface of the water;
a light source attached to the light support member, and configured to direct light to illuminate the target, the lights located below the surface of the water, and wherein the light source and camera are configured such that light emanating from the light source is generally orthogonal to a line of sight of the camera.

2. The floating monitoring apparatus of claim 1, further comprising:
a rod attached to the base.

3. The floating monitoring apparatus of claim 2, wherein the rod is rotatably attachable to the base.

4. The floating monitoring apparatus of claim 1, wherein the light source is at least one LED light.

5. The floating monitoring apparatus of claim 1, wherein the base has a camera hole in optical communication with the camera, to allow the camera to have a field of view below the base.

6. The floating monitoring apparatus of claim 1, wherein the base comprises:
 a first attachment member located on a first end of the base;
 a second attachment member located on an opposite end of the base from the first end;
 a first flotation connecting member attached to the first and second attachment members;
 the first flotation device attached to a first flotation holder, the first flotation holder attached to the first flotation connecting member;
 a second flotation device attached to a second flotation holder, the second flotation holder attached to the first flotation connecting member.

7. A floating monitoring system comprising:
 a volume of water;
 a base, the base comprising an opening rigidly located in the base, and the base configured to be located generally above the surface of the volume of water;
 a first flotation device nonrotatably attached to the base and located generally below the base, the flotation device a non-inflatable rigid pontoon style flotation device configured to float on the surface of water, wherein the base is configured to be nonrotatable with respect to the flotation device;
 a light support member extending downward from the base, and configured to be at least partially below the surface of water;
 a camera nonrotatably attached to the base and configured to be aimed through the opening to capture images of a target below the base, wherein the camera is generally kept above the surface of the water;
 a light source attached to the light support member, and configured to direct light to illuminate the target, the lights located below the surface of the water, and wherein the light source and camera are configured such that light emanating from the light source is generally orthogonal to a line of sight of the camera;
 a rod, with a first end and a second end, the first end of the rod rotatably attached to the base;
 a structure located outside of the volume of water, the second end of the rod rotatably attached to the structure.

8. The floating monitoring system of claim 7, further comprising:
 a power supply located near the structure;
 a first cable in communication with the camera, the cable running from the camera up the rod to the power supply.

9. The floating monitoring system of claim 7, further comprising:
 a power supply located near the structure;
 a first cable in communication with the light source, the cable running from the light source up the rod to the power supply.

10. The floating monitoring system of claim 8, further comprising:
 a computer in communication with the first cable, the computer configured to receive the data from the camera.

11. A monitoring apparatus comprising:
 a base configured to sit on top of a jar;
 a first side extending downwardly from the base, and configured to be located on the outside of the jar;
 a second side extending downwardly from the base, and configured to be located on the outside of the jar;
 a third side extending downwardly from the base, and configured to be located on the outside of the jar;
 a camera housing located on the first side, the camera housing comprising an opening rigidly located in the camera housing, the camera housing configured to be rigid and nonrotatable with respect to the base and first side;
 a camera nonrotatably attached to the camera housing, the camera configured to view through the opening a target located inside the jar;
 a light source located on the second side, the light source configured to illuminate a target inside the jar;
 wherein the light source and camera are configured such that light emanating from the light source is generally orthogonal to a line of sight of the camera.

12. The monitoring apparatus of claim 11, further comprising:
 a clearance opening located in the base.

13. The monitoring apparatus of claim 11, wherein the camera is in signal communication with a computer.

* * * * *